United States Patent [19]

Boochard

[11] Patent Number: 4,853,973
[45] Date of Patent: Aug. 8, 1989

[54] WELDING HELMET

[75] Inventor: E. L. Boochard, Kent City, Mich.

[73] Assignee: Jackson Products, Inc., Belmont, Mich.

[21] Appl. No.: 169,887

[22] Filed: Mar. 18, 1988

[51] Int. Cl.$^4$ ............................................. A61F 9/06
[52] U.S. Cl. ............................................. 2/8; 2/434
[58] Field of Search ............... 2/8, 6, 10, 424, 432, 2/9, 434

[56] References Cited

U.S. PATENT DOCUMENTS

| | | |
|---|---|---|
| 2,406,092 | 8/1946 | Meyer ................................ 2/8 |
| 3,276,034 | 10/1966 | Cupp ................................. 2/8 |
| 3,868,727 | 4/1975 | Paschall ............................. 2/8 |
| 3,890,646 | 6/1975 | Fassett et al. ...................... 2/8 |
| 4,011,594 | 3/1977 | Guilbaud et al. ................... 2/8 |
| 4,193,132 | 3/1980 | Peterson ............................ 2/8 |
| 4,422,185 | 12/1983 | Cook ................................. 2/8 |
| 4,523,808 | 6/1985 | Miller et al. ..................... 350/146 |

FOREIGN PATENT DOCUMENTS 0537469 11/1931 Fed. Rep. of Germany ............... 2/8

Primary Examiner—Peter Nerbun
Attorney, Agent, or Firm—Woodcock, Washburn, Kurtz, Mackiewicz & Norris

[57] ABSTRACT

Disclosed is a welding helmet that provides two levels of protection to the eyes and face of the helmet user. The helmet comprises a protective shell having an opaque front wall extending in the front of the face of the wearer and two side walls extending rearwardly from the front wall along the sides of the face of the wearer. The front wall includes a relatively transparent viewing means for allowing the wearer to see beyond the front wall. A visor is attached to the helmet for removably covering the viewing means of the shell with a relatively protective welder's glass. The helmet generally includes means contained sustantially within the protective shell for mounting the visor to the protective shell. According to certain embodiments, the means for mounting the visor includes the visor having a connection arm with the first end and a second end. The connecting arm is pivotally mounted at a point intermediate first end and the second end to one of the side walls of the shell. The first end of the connecting arm is fixedly connected to the visor while the second end is resiliently connected to the shell.

21 Claims, 3 Drawing Sheets

WELDING HELMET

The present invention is related by subject matter to Design Application Ser. No. 169,752 (Attorney's Docket No. JAC-3), assigned to the assignee of the present invention and filed concurrently herewith.

The present invention relates to welding helmets, and in particular to helmets having two stages of protection for the welder's eyes.

Many types and styles of welding helmets are known. According to one conventional helmet design, a protective shell is pivotally attached to a head band that fits around the wearers head. A viewing window is formed in that portion of the shell adjacent to the welder's eyes. A welder's filter glass especially formulated to filter out the dangerous wavelengths of light produced during the welding process is permanently fitted into the window. Due to the nature of the filter glass, the total amount of light that passes through the glass to the welder's eyes is greatly reduced, thereby making it difficult or impossible for the welder to see in ordinary light. Accordingly, the shell is pivotally mounted to the head band so that the welder can move the helmet into and out of operative position. Thus, the welder must pivot the entire shell on the head band in order to remove the welder's glass from his line of sight, which he must frequently do in order to complete all those tasks ancillary to the welding process, such as inspecting his work and chipping slag from a weld. Although such helmets are generally efficacious for the intended purpose, they suffer from several disadvantages. For example, the protective shell is susceptible to unanticipated and unwanted movement from the raised position to the lowered position as a result of gravity. Moreover, the wearer must move the entire helmet is order to remove the filter glass from his field of view. Such a requirement is not only burdensome, it creates an enlargement of the helmet that is undesirable when welding is being performed in locations with restricted access.

In other styles of welding helmet, the welder's glass is mounted on a pivoting visor which is moveable to a covering position with respect to the opening in the protective shell. Such visors are typically hinged at their top edge to the shell, thereby allowing the glass to pivot into a position outside the welders field of view. Due to the configuration of helmets of this type, however, the welder's glass is generally of a relatively small size (2 inches by 4.5 inches) so that the hinge can maintain the visor in the raised position against the pull of gravity. Although such a helmet overcomes some of the disadvantages described above, it still produces an unwanted expansion of the size of the helmet. Moreover, when the welder raises the visor to inspect his work, his/her eyes are exposed to the danger of hot, flying or chipped slag.

U.S. Pat. No. 4,422,185 -Cook relates to a welding helmet that is said to overcome some of the disadvantages described above. The helmet disclosed in the Cook patent comprises a face protective hood pivotally mounted to a head band that is mountable to the welder's head. A visor for carrying the welder's glass is located in front of the hood and mounted to the hood for swinging upwardly and downwardly. The visor includes a front portion which extends across the front of the hood and a right and a left side which extend rearwardly along the outside of the hood. The visor is attached to the hood on both the left and right side by pivot bolts. The helmet includes a chin strap which has generally vertical right and left side portions attached respectively to the left and right side portions of the visor rearward of the pivot bolt. An angular spring is connected to the visor and the hood at points of the pivot point of the visor. During operation of the helmet, downward pressure of the operators chin on the chin strap causes a downward force on the back end of the visor. This downward force in turn results in an upward movement of the front end of the visor. Once the visor is moved passed a certain point, the force of the spring is said to cause the visor to move to the full raised position. A clear viewing plate is included in the opening in the hood to protect the wearers eyes when the visor is in the fully raised position. Although the Cook patent overcomes some of the disadvantages described above, there are several undesirable features attendant to this design. For example, the Cook helmet requires a complex and awkward chin strap mechanism in order to raise the visor to the raised position. Moreover, the manner in which the visor is mounted to the outside of the hood produces a large number of irregularities and discontinuities in the outer shell surface. Such a configuration is not only aesthetically unpleasing, it results in ledges, flat areas and gaps that tend to catch hot slag spattered about during the welding process. Once caught in these gaps and other irregularities, the hot slag can eventually burn through the helmet. This latter problem is especially relevant for helmets which are made of thermoplastic materials, as is the modern trend. Disadvantages are also associated with the visor lift mechanism provided by the Cook patent. In particular, the spring lift mechanism of the Cook helmet is relatively difficult to manufacture and/or repair. Moreover, the lift mechanism is fully exposed and unprotected when the visor is in the raised position. Such a configuration is undesirable because it detracts greatly from the aesthetics of the helmet and it is unsafe because it creates yet another area which is liable to catch hot slag.

It is an object of the present invention to overcome the disadvantages of heretofore known welding helmets, including those of the type described above. In particular, it is an object of the present invention to provide two levels of protection to the eyes and face of the helmet user.

It is a further object of the present invention to provide a visor lift mechanism which is capable of maintaining relatively large size visors (4 inches × 5.5 inches) in the raised or open position without unwanted and/or anticipated movement of the visor to the lowered or closed position, while simultaneously ensuring that the visor is kept in the lowered position during the welding operation.

It is yet another objection of the present invention to provide a welding helmet having a visor with a lift mechanism that exposes no ledges, flat areas or other substantially discontinuous surfaces.

It is still a further object of the present invention to enclose the lift assist mechanism of the visor within the protection of the outer shell.

These and other objects of the present invention are provided by a helmet comprising a protective shell having an opaque front wall extending in front of the face of the wearer and two side walls extending rearwardly from said front wall along the sides of the face of the wearer, said front wall including relatively transparent viewing means for allowing the wearer to see beyond the front wall. Attached to the helmet is a visor means for removable covering the viewing means of the shell with a relatively protective welder's glass. According to certain embodiments of the present invention, the visor means also includes means for protecting the top of the welders head. The helmets of the present invention also generally include means contained substantially within the protective shell for mounting the visor means to the protective shell. According to certain embodiments of the present invention, the means for mounting the visor includes said visor having a connecting arm with a first end and a second end. The connecting arm is pivotally mounted at a point intermediate the first and second ends to one of the side walls of the shell. The first end of the connecting arm is fixedly connected to the visor. Also provided is means for resiliently connecting the second end of the connecting arm to the side wall, said resilient means resisting movement of the visor from the lowered position to the raised position and from the raised position to the lower position.

DETAILED DESCRIPTION OF A PREFERRED EMBODIMENT

Figure 1:
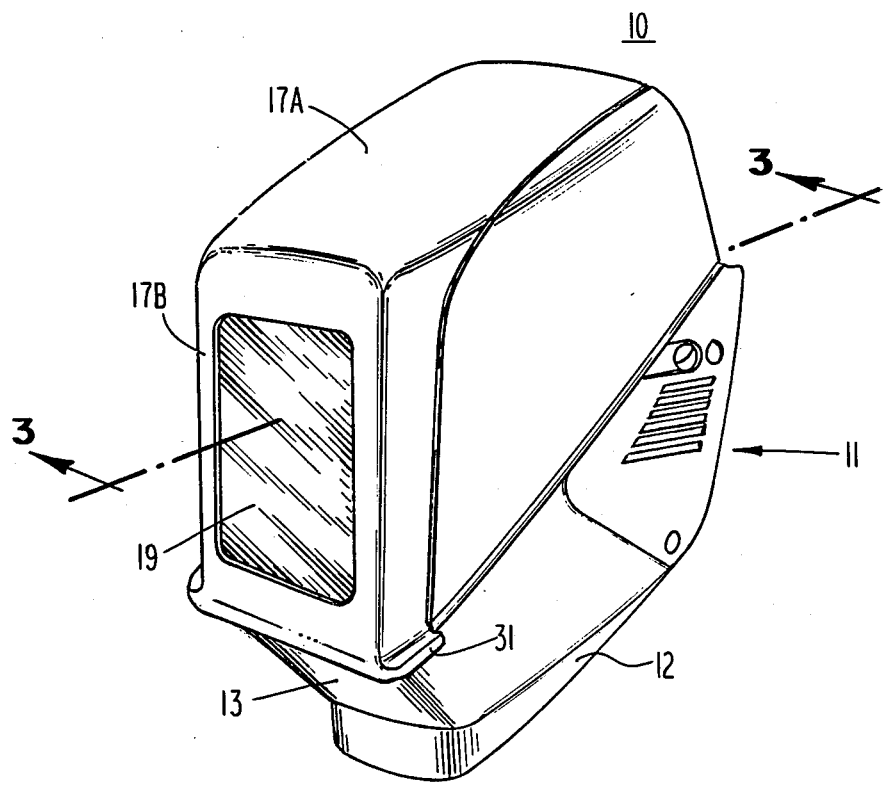
FIG. 1 is a front perspective view of a helmet according to one embodiment of the present invention, the visor of the helmet being in the lowered or closed position.
Figure 2:
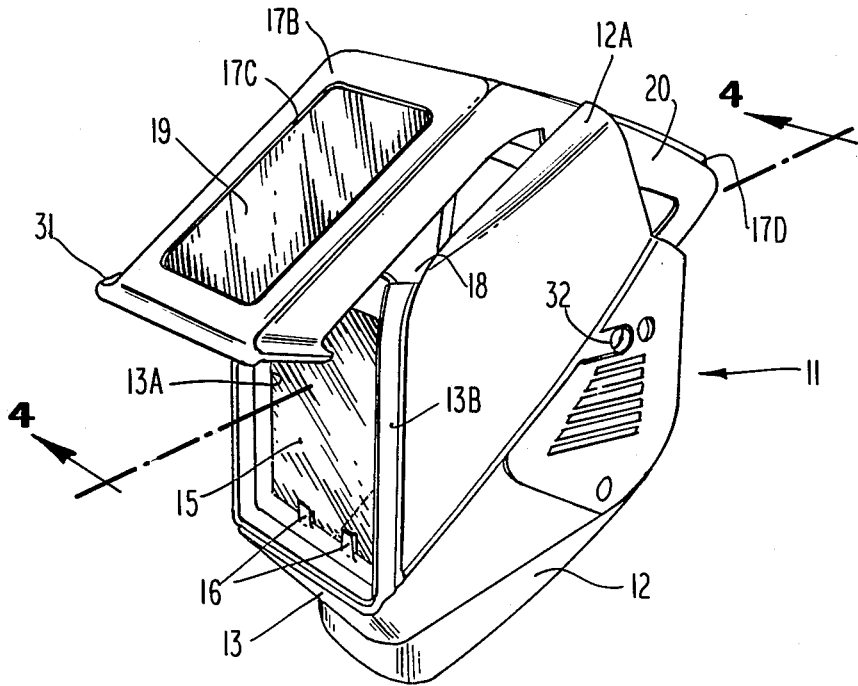
FIG. 2 is a front perspective view of the welding helmet shown in FIG. 1 with the visor in the raised position.

With particular reference now to FIGS. 1 and 2, a welding helmet according to one embodiment of the present invention will be described. As is particularly evident from the drawing of FIG. 1, the welding helmet 10 according to a preferred embodiment of the present invention has an outward appearance that is relatively smooth and aesthetically appealing. Such a characteristic is provided, at least in part, by a protective shell 11 that forms an opening adapted to receive the head of the wearer. The helmet 10 is mountable on the wearer's head by head band 50, which is partially contained within the shell and which pivotally attached to the helmet via aperture 51. The protective shell 11 includes a left side wall 12, a front wall 13 and a right side wall 14. The protective shell 11 is made primarily of a protective opaque material, preferably opaque thermoplastic. The side walls 12 and 14 extend rearwardly from the front wall 13 and are adapted to cover the sides of the welders face and head. In operation, the front wall 13 is in front of and adjacent to the face of the wearer. An opening or window 13A is provided in the front wall 13 of the protective shell 11 so that the weider can see beyond the opaque front wall to the welding area. According to a preferred embodiment of the present invention, opening 13A is covered by a relatively transparent protective glass 15 mounted to front wall 13 of shell 11. In a preferred embodiment, the protective glass is about 5 inches high, about 4.5 inches wide and is mounted to the front wall 13 by four tabs 16, two of which extend upwardly from the front wall 13 and two of which extend downwardly from the front wall. The viewing glass 15 is slightly larger than the opening in the front wall 13 and accordingly the tabs 16 maintain the viewing glass 15 in a stable position in the front wall portion 13 of the shell 11. According to a preferred embodiment of the present invention, viewing glass 15 is a transparent viewing glass which allows passage of all wavelengths of light.

Figure 3:
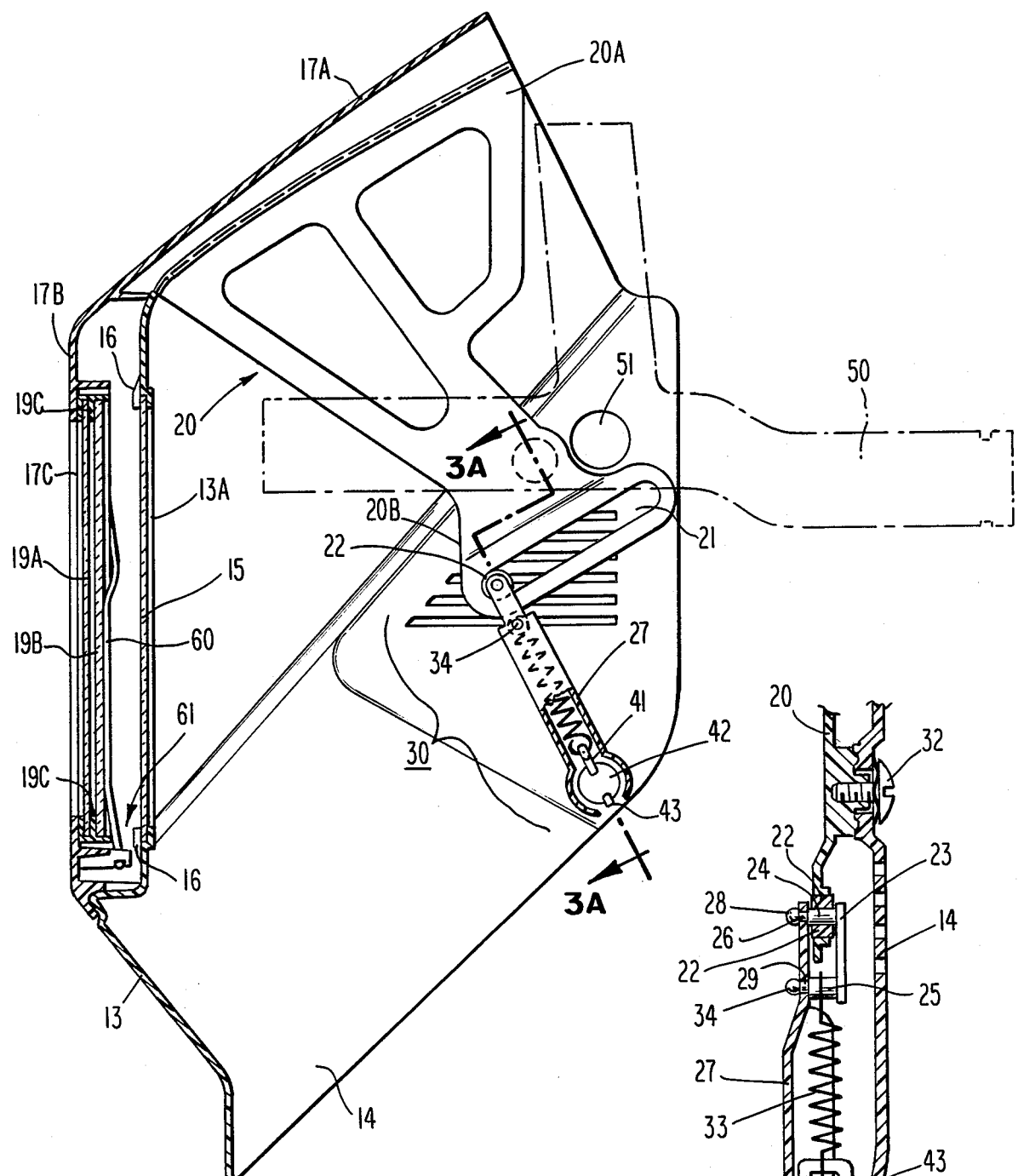
FIG. 3 is a cross sectional view taken substantially along lines 3—3 of FIG. 1.
Figure 4:
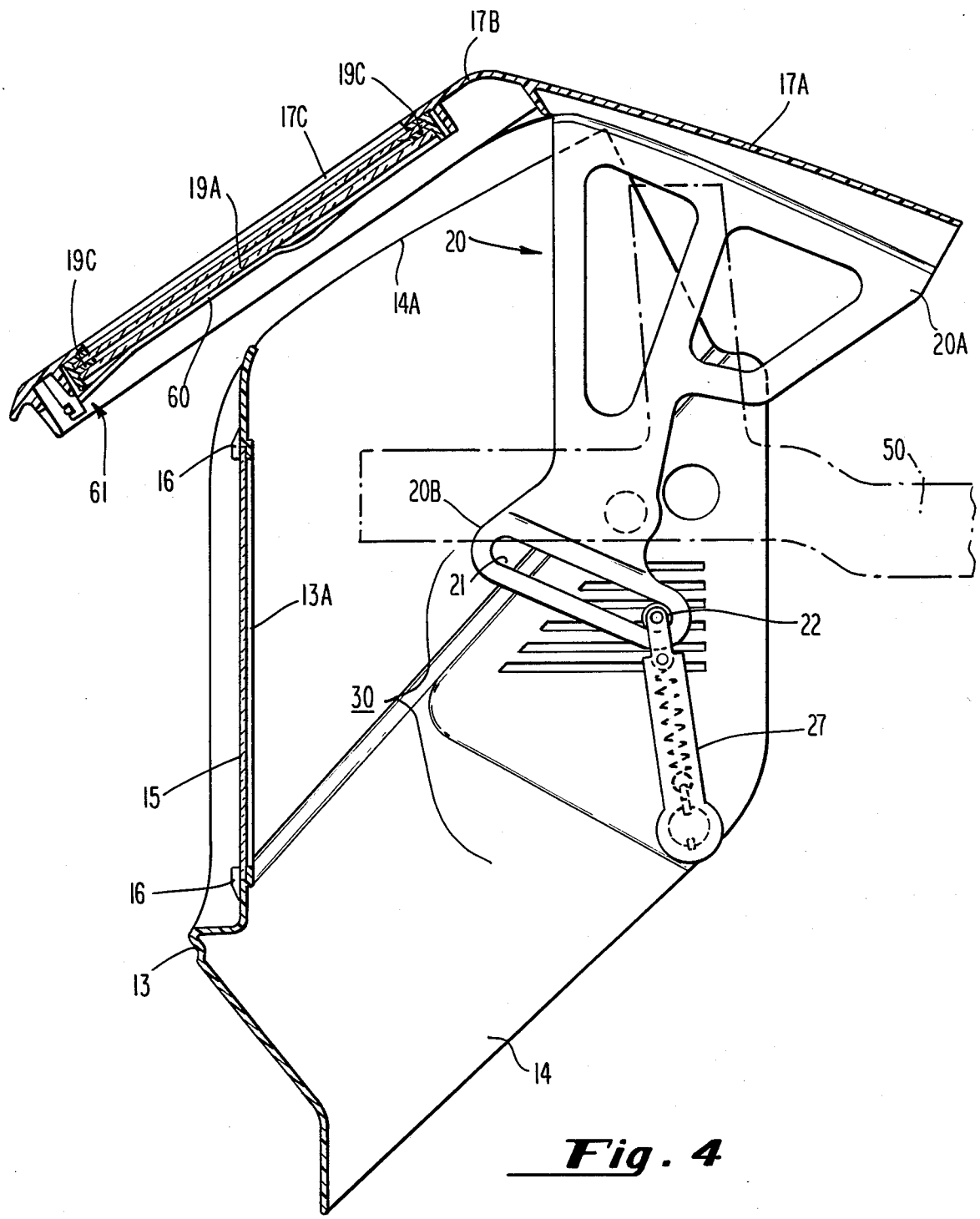
FIG. 4 is a cross sectional view taken substantially along lines 4—4 of FIG. 2.

The helmet of the present invention includes a visor 17 adapted to alternatively cover and uncover opening 13A in the front wall 13. As best revealed in FIG. 1, the visor 17 is adapted to completely cover the opening 13A when the visor is in the lowered or closed position. According to a preferred embodiment, visor 17 not only closes the opening in the front wall 13 of the shell 11, it also closes the opening 18 in the top portion of the shell. In particular, the visor 17 includes a top portion 17A which closes the opening 18 when the visor is in the closed or lowered position. The front face 17B of visor 17 includes an opening 17C through which the welder may view the welding operation when the visor is in the closed position. According to a preferred embodiment of the present invention, the opening 17C is covered by means 19 for protecting the welder's eyes from the intense light produced during the welding operation, said means preferably comprising a dark welders filter glass. According to the embodiment depicted in the drawing Figures, the means for protecting 19 includes a composite or "stack-up" of two or more protective plates. With particular reference to FIGS. 3 and 4, the stack-up comprises a relatively clear outer protective plate 19A and a dark welder's glass 19B. The plates are separated by gasket 19C. Welder's glass 19B is preferably comprised of material that is relatively non-transparent with respect to viewing glass 15. Plates 19A and 19B are mounted to visor 17 by any suitable means available to those skilled in the art, such as by high strength adhesive. It is preferred, however, that the stack-up 19 be removably mounted to visor 17, such as by a spring loaded wire bale 60, said wire bale being hingedly mounted to visor 17 at its upper end and releasable attached to the visor at its lower end by a clip and socket mechanism as indicated at 61.

The helmet described with respect to FIGS. 1 and 2 provides two stages of protection for the welder's eyes. The first stage of protection is provided by viewing glass 15 which is preferably permanently mounted to the shell 11 and which preferably is transparent to substantially all wavelengths of light. This first stage of protection allows the welder to easily view those tasks ancillary to the actual welding operation while protecting the eyes of the welder from physical harm during those potentially dangerous tasks. This stage of protection is operative when the visor 17 is in the raised or upper position, as shown in FIG. 2. The second stage of protection is provided when visor 17 is in the closed or lowered position, as shown in FIG. 1. This stage of protection is provided, in part, by the dark welder's glass 19, which protects the welder not only from flying slag but also from the harmful high intensity light typically produced during welding operations.

Another important aspect of the present invention resides in the contour and/or shape of the protective shell 11. As can be seen from an examination of FIGS. 1 and 2, the outer contour of the protective shell 11 is relatively smooth and aesthetically appealing, with few, if any, discontinuities. Moreover, the entire helmet has an aesthetically appealing smooth outer surface when the visor 17 is in the closed position as shown in FIG. 1. These desirable characteristics are provided, at least in part, by the visor mounting means of the present invention. In particular, the means for mounting the visor to the protective shell 11 is preferably adapted to be contained substantially within the protective shell when the visor is in the closed position, as shown in FIGS. 1 and 3. As used herein, the terms "interior of the protective shell" and "inside the protective shell" refer to that area contained behind front wall 13 and between side walls 12 and 14. Applicant has found that such a configuration is preferably achieved by providing visor 17 with a connecting means that passes into the interior portion of the shell 11. In the embodiment shown in the drawings, the connecting means comprises a pair of connecting arms 20 which are integral with or otherwise attached to the top portion 17A of the visor 17. In order to maintain a sleek and relatively flat outer shell configuration when the visor 17 is in the down or closed position, applicant has found that it is desirable for connecting arms 20 to enter the interior portion of shell 11 through the three sided opening or cut-out 18 in shell 11, said opening being defined by the upper ends of front wall 13, right side wall 14 and left side wall 12. In this way, left side wall 12, front wall 13 and right side wall 14 can be formed from a single mold and imparted with smooth sleek features. Since the visor 17 enters the shell from above the front wall 13 and from between the side walls 12 and 14, holes or slots are not required in the front or sides of the outer shell to allow entry of the visor into the interior portion thereof.

Applicant has also found that the sleek and smooth shape of the helmet 10 is preferably enhanced by providing sidewalls 12 and 14 with upper ends 12A and 14A which are rounded and curved slightly inward, that is, toward one another, at the top. It is also preferred that the visor 17 have an indented or stepped portion 17D located at about the transition between top portion 17A and connecting arm 20, said indent being adapted to mate with the rounded upper ends 12A and 14A of side walls 12 and 14. The transition between the front wall 13 and the side walls 12 and 14 includes an outwardly extending lip 13B. This lip is adapted to engage a groove which runs along the interior of the front face 17B of the visor 17. Provision of the features described above enhance not only the sleek and smooth appearance of the helmet, they provide a firm and stable fit between the visor 17 and the shell 11 when the visor is in the closed positioned.

Welding helmets according to preferred embodiments of the present invention include mounting means for pivotally mounting the visor 17 to protective shell 11 for movement between a lowered position and a raised position. The lowered position is generally characterized by protective means 19 of the visor 17 substantially covering the viewing opening 13A in front wall 13 of shell 11. The raised position is generally characterized by protective means 19 or visor 17 being in a substantially noncovering position with respect to the viewing opening 13A in the front wall 13 of shell 11. The mounting means of the present invention also preferably include means for resisting movement of said visor from the lowered position to the raised position and from the raised position to the lowered position. In certain preferred embodiments, the mounting means includes lift assist means for urging the opening of said visor from said closed position to said open position over at least some portion of the travel of said visor from said closed position to said open position. That is, it is preferred that the mounting means, although initially resisting movement of the visor form the fully closed position to the open position, subsequently assists movement to the open portion. It is also preferred that the converse is true. In particular, the mounting means, although initially resisting movement of the visor form the open position to the closed position, subsequently assists movement to the closed position.

Figure 3A:
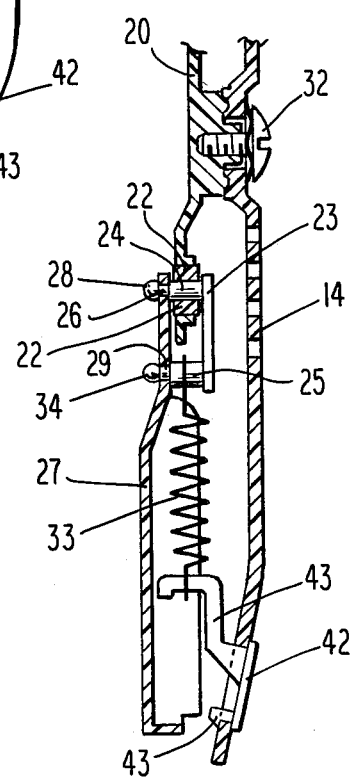
FIG. 3A is a cross sectional view taken substantially along lines 3A—3A of FIG. 3.

A preferred means for pivotally mounting visor 17 to shell 11 will now be described with respect to FIGS. 3, 3A and 4. The visor mounting means of the present invention generally includes a connecting arm, preferably a pair of connecting arms, depending from the top portion 17A of the visor 17. The connecting arms, labeled as 20 in the embodiment shown in the drawing Figures, are pivotally mounted to the protective shell 11 by pivot bolt 32. The mounting means of the illustrated embodiment also includes resilient means, generally designated as 30 in FIGS. 3, 3A and 4, connected between connecting arm 20 and shell 11 for applying a moment arm to connecting arm 20. As used herein, the term moment arm refers to any force applied to connecting arm 20 that tends to urge the connecting arm to pivot about its pivot point, that is, the point at which arm 20 is pivotally attached to shell 11. A moment arm is generally produced by applying to arm 20 a force that contains at least some component of force which does not pass through the pivot point of arm 20.

Although the embodiment shown in the drawing Figures includes a set of substantially parallel connecting arms 20 depending form each side of the top portion 17A of visor 17, the pivotal mounting means and the resilient means are described in detail herein only with respect to right side wall 14, attachment to the other side wall being substantially identical. As seen in FIG. 3, the visor mounting means according to a preferred embodiment of the present invention comprises a connecting arm 20 having a top end 20A and a bottom end 20B. The top end 20A of connecting arm 20 is integral with or otherwise attached to the top 17A of visor 17. Connecting arm 20 is pivotally mounted by pivot bolt 32 to side wall 14 at a point intermediate said top end 20A and said bottom end 20B of connecting arm 20. Resilient connecting means 30 includes the lower end 20B of connecting arm 20 having an elongate slot 21 therein. In the embodiment of the Figures, the axis of elongate slot 21 slopes downward from the rear of the protective shell 11 towards the front wall 13 when the visor 17 is in the closed position, and upward from the rear of the protective shell towards the front wall when the visor is in the open position. Contained within slot 21 is a roller 22 or some similar means for achieving relatively frictionless movement therealong. A link plate 23 provides means for connecting roller 22 to a force means such as helical spring 33. Link plate 23 includes a first cylindrical projection 24 which passes concentrically through roller 22. A narrowed cylindrical portion 26 depends from projection 24 and passes through an aperture in spring cover member 27. The first cylindrical projection 24 is provided with a bulbus end 28 which serves to hold the cover plate 27 in place. A second cylindrical projection 25 extends from the lower portion of link plate 23. The lower cylindrical member 25 also includes a narrowed cylindrical portion 29 which passes through a second aperture in cover plate 27. A bulbus portion 34 is also included on the end of projection 25. The combination of link plate 23 and cover plate 27 thus provides means for connecting one end of spring 33 to roller 22. Moreover, cover plate 27 also protects the wearer's head from spring 33.

In a preferred embodiment of the present invention, the apertures in the cover plate 27 are circular apertures of variable diameter, the diameter being responsive to the exertion of substantial axial pressure thereon. In this way the cover plate can be readily passed over the bulbous ends 28 and 34, thus facilitating the assembly and disassembly of the resilient means of the present invention.

The upper end of spring 33 is connected to cylindrical projection 25 of link plate 23. The lower end of spring 33 is connected to side wall 14 by connecting means 40. Connecting means 40 includes a hooked portion 41, a mounting plate 42 and a detented tab 43. Hooked portion 41 is mounted on mounting plate 42 and provides a member to which the lower end of spring 33 is attached. Tab 43 is resiliently mounted on mounting plate 42 for movement between a non-interfering position with respect to that portion of side wall 14 which forms the edge of opening 45 and an interfering position with respect to that portion of the side wall. In a preferred embodiment, aperture 45 is a circular aperture having a diameter less than the diameter of backing plate 42. In this way, connecting means 40 is removably attached to side wall 14, thus facilitating assembly and repair of the resilient means of the present invention.

Roller 22 provides means for transmitting the downward force of spring 33 to the lower end 20B of connecting arm 20. Thus, resilient means 30 provides means for exerting force on the lower end 20B of connecting arm 20. Resilient connecting means 30 is adapted to exert at least some component of force normal to the axis of slot 21. Since roller 22 is contained in the forward end of slot 21 when the visor is in the closed position, resilient means 30 exerts a moment arm on connecting arm 20 that tends to urge the visor into the closed position. Moreover, slot 21 is oriented such that roller 22 will move from one end of the slot to the other end of the slot as the visor 17 is moved between the fully closed position and the fully raised position. In the closed position as shown in FIG. 3, the resilient connecting assembly 30 provides a normal component of force to connecting arm 20 at a location which is forward of the point at which the connecting arm is pivotally mounted to the shell 11, thus tending to pivot arm 20 in a counter clockwise direction. Due in part to the orientation of a slot 21, resilient assembly 30 holds the roller 22 in the forward end of the slot when the visor is in the closed position while simultaneously providing a force to connecting arm 20 that resists movement of the visor 17 from the closed position. During operation, the wearer of the mask raises the visor by using the hand assist tabs 31 (shown in FIG. 1) to move the visor up and away from the viewing glass 15. This movement of the visor causes the forward end of slot 21 to move up and forward. Due to the relative location of slot 21 and resilient assembly 30, this first movement of the visor is initially resisted by the resilient assembly. However, upon further movement of the visor 17, roller 22 will tend to slide or roll towards the rearward end of slot 21, and the resistance to upward movement of the visor 17 decreases until the roller 22 travels to a point at which it is collinear with the pivot point of the connecting arm and the point at which spring 33 is attached to the connecting means 40. At this point, resilient means 30 experts no component of force on connection arm 20 that does not pass through the pivot point. Further movement of the visor past this colinearity point will cause roller 22 to travel to the rearward end of slot 21 and thereby urge the visor 17 into the open position as shown in FIG. 4. In the open position as shown in FIG. 4, the resilient connecting means 30 provides a normal component of force to the connecting arm 20 at a location which is rearward of the point at which the connecting arm is pivotally mounted to shell 11, thus tending to move arm 20 in a clockwise direction. Due in part to the orientation of slot 21, resilient means 30 holds roller 22 in the rearward end of the slot when the visor is in the open position while simultaneously providing a force to connecting arm 20 that resists movement of the visor from the open position. In this way, the visor mounting means of the present invention is capable of maintaining relatively large size welder's glass in the raised position without unwanted or unanticipated movement of the visor to the closed position. The visor can be returned to the closed position by an external force sufficient to overcome the force of spring 33, such as a sharp downward nod of the welder's head.

What is claimed is:

1. A welding helmet of the type having a protective shell with an opening therein adapted to receive the head of the wearer, said shell being mountable to the head of the wearer, said helmet comprising:
   (a) a protective shell having an opaque front wall extending in front of the face of the wearer and two side walls extending rearwardly from said front wall along the sides of the face of the wearer, said front wall including relatively transparent viewing means for allowing the wearer to see beyond said front wall;
   (b) a visor for removably covering said viewing means with a relatively non-transparent welder's glass and for protecting the top of said welders head; and
   (c) means contained substantially within said protective shell for mounting said visor to said protective shell for movement between a lowered position in which said welder's glass covers at least a substantial portion of said viewing means and a raised position in which said welder's glass does not substantially cover said viewing means.

2. The welding helmet of claim 1 wherein the exterior of said protective shell is substantially smooth and continuous.

3. The welding helmet of claim 1 wherein said protective shell has an opening at the top thereof, and wherein said visor includes a top portion which closes said opening when said visor is in the lowered position.

4. The welding helmet of claim 3 wherein said means for mounting said visor includes a connecting arm having a first end and a second end, said first end being attached to said visor, said connecting arm being pivotally mounted to one of said side walls at a point intermediate said first end and said second end.

5. The welding helmet of claim 4 wherein said mounting means further includes lift assist means for urging the movement of said visor from said lowered position to said raised position over at least some portion of the travel of said visor from said lowered position to said raised position.

6. The welding helmet of claim 4 wherein said mounting means further includes resilient means for resisting movement of said visor from the lowered position to the raised position and from the raised position to the lowered position.

7. The welding helmet of claim 6 wherein said mounting means further includes lift assist means for urging the movement of said visor from said lowered position to said raised position over at least some portion of the travel of said visor from said lowered position to said raised position.

8. The welding helmet of claim 6 wherein said resilient means is connected between said second end of said connecting arm and said one side wall.

9. The welding helmet of claim 8 wherein said resilient means includes:
   (a) said lower end of said connecting arm having an elongate slot therein;
   (b) means contained within said slot for relatively frictionless movement therealong; and
   (c) means for resiliently connecting said movement means to said side wall.

10. The welding helmet of claim 8 wherein said means for resiliently connecting said movement means to said side wall comprises means for applying a moment arm to said connecting arm.

11. A welding helmet of the type having a protective shell with an opening therein adapted to receive the head of the wearer, said shell being mountable to the head of the wearer, said helmet comprising:
   (a) a protective shell having an opaque front wall portion and two substantially parallel side wall portions extending rearward from the vertical edges of said front wall portion, said front wall including relatively transparent viewing means for allowing the wearer to see beyond said front wall;
   (b) visor means for removably covering said viewing means with a relatively opaque welder's glass; and
   (c) means for mounting said visor means to said protective shell for movement between a lowered position and a raised position, said mounting means including,
      (i) a connecting arm having a first end and a second end, said connecting arm being pivotally connected to one of said walls at a point intermediate said first and second ends, said first end being fixedly connected to said visor means, and
      (ii) means for resiliently connecting said second end of said arm to said side wall, said resilient connecting means resisting movement of said visor from said lowered position to said raised position and from said raised position to said lowered position.

12. The welding helmet of claim 11 wherein the exterior of said protective shell is substantially smooth and continuous.

13. The welding helmet of claim 11 wherein said protective shell has an opening at the top thereof, and wherein said visor includes a top portion which closes said opening when said visor is in the lowered position.

14. The welding helmet of claim 13 wherein said means for mounting said visor is contained substantially within said protective shell.

15. The welding helmet of claim 14 wherein said mounting means further includes lift assist means for urging the movement of said visor from said lowered position to said raised position over at least some portion of the travel of said visor from said lowered position to said raised position.

16. The welding helmet of claim 15 wherein said resilient connecting means includes:
   (a) said lower end of said connecting arm having an elongate slot therein;
   (b) means contained within said slot for relatively frictionless movement therealong; and
   (c) means for resiliently connecting said movement means to said side wall.

17. The welding helmet of claim 15 wherein said means for resiliently connecting said movement means to said side wall comprises means for applying a moment arm to said connecting arm.

18. A welding helmet of the type having a protective shell with an opening therein adapted to receive the head of the wearer, said shell being mountable to the head of the wearer, said helmet comprising:
   (a) a substantially smooth and continuous protective shell having an opaque front wall extending in front of the face of the wearer, and two side walls extending rearwardly from said front wall along the sides of the face of the wearer, the upper ends of said front wall and said side walls defining an opening in the top of said protective shell, said front wall including relatively transparent viewing means for allowing the wearer to see beyond said front wall;
   (b) a visor for removably covering said viewing means with a relatively non-transparent welder's glass, said visor including a top portion; and
   (c) means for mounting said visor to said protective shell for movement between a lowered position in which said welder's glass covers at least a substantial portion of said viewing means and a raised position in which said welder's glass does not substantially cover said viewing means, said visor top portion substantially covering said shell top opening when said visor is in the lowered position.

19. The welding helmet of claim 18 wherein said side walls have rounded upper portions that are curved inward at the top.

20. The welding helmet of claim 19 wherein said means for mounting said visor includes a pair of spaced and substantially parallel connecting arms, each connecting arm having a first end and a second end, said first ends being attached to said top portion of visor, each of said connecting arms being pivotally mounted to a separate one of said side walls.

21. The welding helmet of claim 20 wherein said visor includes indented portions located at about the transition between said connecting arms and said top portion, said indented portions being adapted to mate with said rounded upper portions of said side walls.

* * * * *